United States Patent [19]

Ishii et al.

[11] Patent Number: 4,938,219
[45] Date of Patent: Jul. 3, 1990

[54] ELECTROCARDIOGRAPHIC ELECTRODE

[75] Inventors: Hiroyoshi Ishii; Kenzo Suzuki; Misao Kaneko; Hiroshi Kawamoto, all of Saitama; Chuji Shimizu, Chiba; Yasuaki Onodera, Saitama, all of Japan

[73] Assignees: Fukuda Denshi Co., Ltd.; Kabushiki Kaisha Riken, Tokyo, Japan

[21] Appl. No.: 423,590

[22] Filed: Oct. 17, 1989

Related U.S. Application Data

[63] Continuation of Ser. No. 144,134, Jan. 15, 1988, abandoned.

[30] Foreign Application Priority Data

Jan. 16, 1987 [JP] Japan ................................ 62-004575
Jan. 16, 1987 [JP] Japan ................................ 62-004577

[51] Int. Cl.$^5$ ............................................. A61B 5/0402
[52] U.S. Cl. ...................................... 128/641; 128/640
[58] Field of Search ............... 128/639, 640, 641, 644, 128/802, 803

[56] References Cited

U.S. PATENT DOCUMENTS

| | | | |
|---|---|---|---|
| 2,895,479 | 9/1957 | Lloyd | 128/640 |
| 3,547,105 | 12/1970 | Paine | 128/640 |
| 3,566,860 | 3/1971 | Moe, Jr. | 128/641 |
| 3,713,435 | 1/1973 | Szpur | 128/641 |
| 3,834,373 | 9/1974 | Sato | 128/641 |
| 3,841,312 | 10/1974 | Corasanti | 128/641 |
| 3,845,757 | 11/1974 | Weyer | 128/641 |
| 3,901,218 | 8/1975 | Buchalter | 128/641 |
| 3,976,055 | 8/1976 | Monter et al. | 128/641 |
| 3,982,529 | 9/1976 | Sato | 128/641 |
| 4,270,544 | 6/1981 | Gilden et al. | 128/640 |
| 4,273,135 | 6/1981 | Larimore et al. | 128/640 |
| 4,635,642 | 1/1987 | Cartmell et al. | 128/641 |
| 4,706,680 | 11/1987 | Keusch et al. | 128/641 |

Primary Examiner—Lee S. Cohen
Assistant Examiner—Kennedy Schaetzle
Attorney, Agent, or Firm—Pollock, VandeSande & Priddy

[57] ABSTRACT

An electrocardiographic electrode is disclosed, which comprises an electrode element consisting of a synthetic resin electrode element having a head portion with a lead attached thereto and having a straight recessed portion, a neck portion having an engagement portion narrower than the head portion and capable of being engaged in an expansible member and a straight portion continuous to the straight recessed portion of the head portion and a bottom portion formed under, broader than and supporting the neck portion and to be held in contact with the skin of a living body, the outer surface of the synthetic resin electrode element member being imparted with electric conductivity by coated metal powder, an expansible member engagedly locked in the engagement portion of the neck portion, and an adhesive film consisting of an adhesive, having a central portion and secured to the expansible member to be held in close contact with the skin of the living body.

2 Claims, 2 Drawing Sheets

PRIOR ART

ELECTROCARDIOGRAPHIC ELECTRODE

This application is a continuation of application Ser. No. 144,134 filed Jan. 15, 1988 now abandoned.

BACKGROUND OF THE INVENTION

1. Field of the Invention

This invention relates to an electrocardiographic electrode and, more particularly, to an electrocardiographic electrode comprising an electrode element to be held in close contact with the skin of a man to derive a weak current from the man's body, an expansible member engagedly locked in the electrode element member and an adhesive film, having a central opening and secured to the expansible member to be held in close contact with the skin of the man.

2. Prior Art

Electricity is generated in the living body by the activity of the heart, brain, muscles, etc.

Particularly, electrocardiographic electrodes are used for diagnosing the heart by monitoring a weak current that is induced on the skin of the living body using an external electrocardiograph.

To couple an input section of the electrocardiograph and the living body electrically, it is necessary to have electrocardiographic electrodes in close contact with the skin of the living body.

A prior art electrocardiographic electrode which is held in close contact with the skin of the living body will now be explained with reference to FIG. 4. In the Figure, reference numeral 1' designates an electrode element made of a metal. An expansible member 2' engages and is secured to electrode element 1' between upper and lower clamp members 20 and 21.

The electrode element 1' has a broad bottom portion 13' which is covered by a conductive cover member (not shown). The electrode element 1' derives an electrocardiographic signal from the skin via the conductive cover member.

Such electrode member 1' for an electrocardiographic electrode, however, is made of a metal and is thus heavy. Therefore, it is not suited for being held on the skin. In addition, electrode characteristics are unsatisfactory because of high polarization voltage.

Further, the electrode element 1' has heretofore been manufactured by silver plating. This method of manufacturing the electrode element by silver plating, however, is complicated in procedure as well as being dangerous and requiring high manufacturing cost.

Furthermore, the expansible member 2' engaged in the electrode element 1' requires two clamping members 20 and 21 for holding it in an engaged state.

SUMMARY OF THE INVENTION

An object of the invention is to overcome the drawback arising from the fact that the electrode element 1' is made of a metal and solve the problems in holding the expansible member 2' and electrode element 1' in an engaged state.

To attain the above object of the invention, there is provided an electrocardiographic electrode comprising an electrode element an expandable member and an adhesive film. The electrode element consists of a synthetic resin having a head portion with a lead attached thereto and having a straight recessed portion, a neck portion having an engagement portion narrower than the head portion and capable of being engaged in an expansible member, a straight portion continuous the straight reecessed portion of the head portion and a bottom portion formed under, broader than and supporting the neck portion and to be held in contact with the skin of a living body, the outer surface of the synthetic resin electrode element member being made electrically conductive by coating powder of a metal. The expansible member is engagedly locked in the engagement portion of the neck portion, and an adhesive film consisting of an adhesive, having a central opening and secured to the expansible member to be held in close contact with the skin of the living body.

Since in the above construction according to the invention the neck portion of the electrode element is formed under and narrower than the head portion, the expansible member is reliably locked by engagement.

In addition, since the electrode element has a broad bottom portion, the area of its contact with the skin is increased to provide more satisfactory electric conductivity.

Further, since the head portion has the straight recessed portion and also the neck portion has the straight portion continuous to the straight recessed portion, satisfactory coating of even a small quantity of metal powder can be obtained.

Further, since the electrode element is made of a synthetic resin, it is reduced in weight. Still further, since its outer surface is coated with metal powder, it has electric conductivity.

Furthermore, since the adhesive film has a central opening and is secured to the expansible member engaged in the straight electrode member, the outer periphery of the electrocardiographic electrode is held in close contact with the skin of the living body.

DETAILED DESCRIPTION OF THE PREFERRED EMBODIMENT

Figure 1:
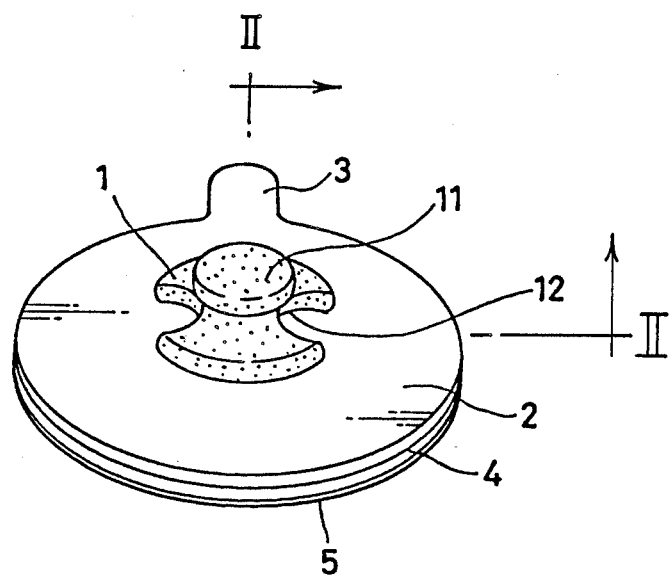
FIG. 1 is a perspective view showing one embodiment of the electrocardiographic electrode according to the invention.

FIG. 1 is a perspective view showing an electrocardiographic electrode according to the invention. In the Figure, reference numeral 1 designates an electrode element. A circular expansible member 2 engages the electrode element 1. The expansible member 2 has a manipulating portion 3 projecting from the edge to facilitate the attachment and detachment of the electrocardiographic electrode with respect to the skin.

An attachment member 4 is attached to the underside of the expansible member 2, and an adhesive film 5 is provided on the underside of the attachment member 4. The viscosity of the adhesive film 5 permits the electrocardiographic electrode to be held in close contact with the skin of a living body.

Figure 2:
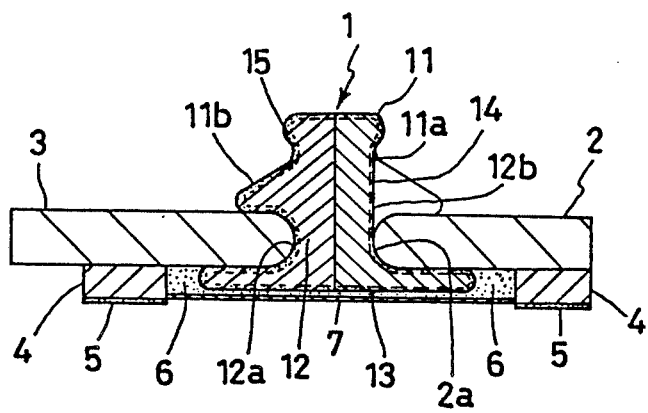
FIG. 2 is a sectional view taken along line II—II in FIG. 1.

FIG. 2 is a sectional view showing one embodiment of the invention. The electrode element 1 has a head portion 11, to which a lead (not shown) is attached, a neck portion 12 formed under the head portion 11 and a bottom portion 13 formed under the neck portion 12. The synthetic resin material 14 is made electrically conductive by coating the outer surface with powder of a metal, e.g., silver or an amorphous alloy, as shown by coating agent 15.

The resin material 14 is a synthetic resin in order to be suited for mass production for cost reduction, for weight reduction to ensure that it is stably held fitted on the skin of a living body and to reduce heat conduction to prevent the sense of coldness of the skin when it is attached thereto. Further, the outer surface of the synthetic resin material 14 is coated with powder 15 of metal in order that the effective area of the outer surface of the material 14 is increased with formation of irregularities, thus improving electrode characteristics.

A lead (not shown) is attached to the head portion 11. The head portion 11 has a straight recessed portion 11a, as shown in FIG. 2.

The neck portion 12 supporting the head portion 11 has an engaged portion 12a narrower than the head portion 11 and a straight portion 12b continuous to and forming a straight surface with the straight recessed portion 11a of the head portion. The engagement portion 12a is provided in order that the expansible member 2 is readily and reliably engaged without use of any clamping members.

The expansible member 2 is formed with a central small hole 2a. When the head portion 11 of the electrode element 1 is inserted through the small hole 2a from below, the small hole 2a is expanded as it is passed by a downwardly and outwardly sloped substantially conoidol section 11b due to the expansibility of the expansible member 2. When the expansible member 2 is fitted up to the narrower neck portion 12, the small hole 2a is contracted by the restoring force due to its own expansibility.

Therefore, the expansible member 2 is readily engaged in the engagement portion 12a of the neck portion 12 of the electrode element and held clamped between the head portion 11 and bottom portion 13.

The head portion is formed with the straight recessed portion 11a and the neck portion is formed with the straight portion 12b continuous to and forming a straight surface with the recessed portion 11a in order that even a small quantity of metal powder can be satisfactorily coated and that satisfactory electric conductivity can be obtained.

Under the neck portion 12, the bottom portion 13 supporting the neck portion 12 is formed such that it is broader than the neck portion 12. Thus, the expansible member 2 engaged in the engagement portion 12a of the neck portion 12 is clamped between the head portion 11 and bottom portion 13.

Figure 3:
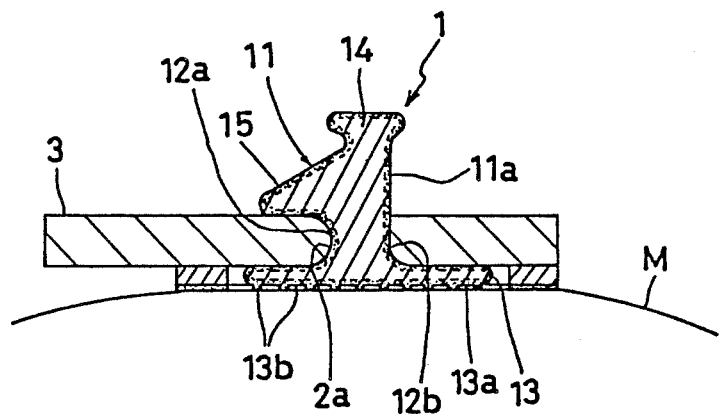
FIG. 3 is a sectional view showing a different embodiment of the electrocardiographic electrode.
Figure 4:
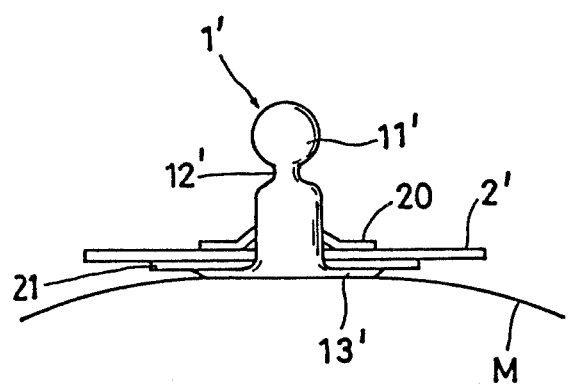
FIG. 4 is a view for explaining the prior art.

The bottom surface 13a of the bottom portion 13, which is held in direct contact with the skin M of the living body, as shown in FIG. 3, has an irregular surface area 13b, thus increasing the contact area and stabilizing the electrode characteristics.

As shown in FIG. 2, near the bottom portion 13 of the electrode element 1 there are a gel-like electrolyte material 6 and an electrolyte material cover 7 covering the electrolyte material 6 for electrical contact with the skin. The electrolyte material 6 fills the space between the electrode element 1 and cover 7 to improve the electrical conductivity.

As has been shown, in the above embodiment of the electrocardiographic electrode the outer surface of the synthetic resin material 14 is coated with the metal powder 15 producing irregularities to increase the effective area. Thus, satisfactory electrode characteristics can be obtained while reducing the weight. With the weight reduction, when the electrode element 1 is held in close contact with the skin, it is held stably on the skin and detached from the skin with difficulty.

Further, since the neck portion 12 is made narrower than the head portion 11 and the bottom portion 13 to form the engagement portion 12a, and the expansible member 2 is engaged in the engagement portion 12a, there is no need of providing any clamping members. It is thus possible to save material, simplify the manufacture and reduce the manufacturing cost.

Further, since the head portion is formed with the straight recessed portion 11a and the neck portion is formed with the straight portion continuous to and forming a straight surface with the recessed portion 11a, the material 14 may be satisfactorily coated with even a small quantity of metal powder 15, and also the electric conductivity is improved.

Further, the electrocardiographic electrode can be reliably held in close contact with the skin of the living body by the attachment member 4 with the adhesive film 5.

Further, near the bottom portion 13 of the electrode element 1 there are provided the gel-like electrolyte material 6 and electrolyte material cover 7 covering the electrolyte material 6, thus improving the conduction of electricity with respect to the skin.

Further, since the electrode element is made of a synthetic resin material, it is possible to reduce cost by mass production. This means that it is possible to improve the sanitation by providing consummable electrocardiographic electrodes. Further, it is possible to reduce heat conduction so as to prevent the sense of coldness when the electrode is attached to the skin.

Furthermore, since the attachment member having a central opening is secured to the expansible member and the adhesive film is secured to the expansible member, the electrocardiographic electrode can be stably held in close contact with the skin of the living body.

What is claimed is:

1. An electrocardiographic electrode comprising:
   (a) a metal-powder coated synthetic resin electrode element comprising a head portion for attachment to an electrical lead, a bottom portion for contacting the skin of a living body, and a neck portion connecting said head portion with said bottom portion and forming an engagement section of said electrode element for engaging an expansible sheet-like member, said head portion having a downwardly and outwardly sloped substantially conoidal section, said conoidal section having at least one recessed portion which forms a continuous vertical surface with said neck portion;
   (b) an expansible sheet-like member having upper and lower surfaces and a central opening engaging said neck portion of said electrode element, said bottom portion of said electrode element and said conoidal section being arranged to support said sheet-like element between them; and,
   (c) an adhesive film secured to said lower surface of said expansible member for retaining said electrocardiographic electrode on the skin of a living body.

2. The electrocardiographic electrode according to claim 1, wherein said bottom portion has an irregular bottom surface area for contact with the skin of the living body.

* * * * *

UNITED STATES PATENT AND TRADEMARK OFFICE
CERTIFICATE OF CORRECTION

PATENT NO. : 4,938,219
DATED : July 3, 1990
INVENTOR(S) : Hiroyoshi Ishii, et al.

It is certified that error appears in the above-identified patent and that said Letters Patent is hereby corrected as shown below:

Column 1, line 63, change "expandable" to --expansible--.

Column 2, line 1, after "continuous" insert --with--.

Column 3, line 62, change "electrical conductivity" to

--electric conductivity--.

Signed and Sealed this

Twelfth Day of May, 1992

Attest:

DOUGLAS B. COMER

*Attesting Officer*   Acting Commissioner of Patents and Trademarks